US010828479B2

(12) United States Patent
Ueno et al.

(10) Patent No.: US 10,828,479 B2
(45) Date of Patent: Nov. 10, 2020

(54) MICROPROJECTION IMPLEMENT AND METHOD FOR PRODUCING SAME

(71) Applicant: Kao Corporation, Tokyo (JP)

(72) Inventors: Satoshi Ueno, Utsunomiya (JP); Hideo Kobayashi, Mooka (JP); Takatoshi Niitsu, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 229 days.

(21) Appl. No.: 15/744,632

(22) PCT Filed: Aug. 5, 2016

(86) PCT No.: PCT/JP2016/073052
§ 371 (c)(1),
(2) Date: Jan. 12, 2018

(87) PCT Pub. No.: WO2017/030012
PCT Pub. Date: Feb. 23, 2017

(65) Prior Publication Data
US 2018/0185624 A1  Jul. 5, 2018

(30) Foreign Application Priority Data

Aug. 19, 2015 (JP) ................................ 2015-162242

(51) Int. Cl.
A61M 37/00 (2006.01)
B29C 51/08 (2006.01)
(Continued)

(52) U.S. Cl.
CPC ......... A61M 37/0015 (2013.01); B29C 51/08 (2013.01); B29C 51/30 (2013.01);
(Continued)

(58) Field of Classification Search
CPC ...... A61M 37/0015; A61M 2037/0023; A61M 2037/003; A61M 2037/0046
See application file for complete search history.

(56) References Cited

U.S. PATENT DOCUMENTS 5,250,067 A * 10/1993 Gelfer ................. A61H 39/00
606/185
6,256,533 B1  7/2001 Yuzhakov et al.
(Continued)

FOREIGN PATENT DOCUMENTS

CN  102553064 A  7/2012
JP  2003-501162 A  1/2003
(Continued)

OTHER PUBLICATIONS

International Search Report issued in PCT/JP2016/073052 (PCT/ISA/210), dated Oct. 25, 2016.

Primary Examiner — Laura A Bouchelle
(74) Attorney, Agent, or Firm — Birch, Stewart, Kolasch & Birch, LLP

(57) ABSTRACT

A microprotrusion device (1A) according to the present invention includes a needle-like and hollow first protrusion portion (3) that is formed so as to protrude from one surface (2a) of a substrate sheet (2) and a hollow second protrusion portion (4) that is formed so as to protrude from a vicinity of the first protrusion portion (3) on the one surface (2a) of the substrate sheet (2) and has a protrusion height lower than that of the first protrusion portion (3). The first protrusion portion (3) has an opening at its tip end portion, and a hollow portion (30) of the first protrusion portion (3) is in communication with the outside via the opening portion (31). The opening portion (31) is formed at the tip end of the first protrusion portion (3).

11 Claims, 8 Drawing Sheets

(51) Int. Cl.
  B29C 51/42 (2006.01)
  B29C 51/32 (2006.01)
  B29C 51/30 (2006.01)
  B29K 67/00 (2006.01)
  B29K 77/00 (2006.01)
  B29K 23/00 (2006.01)
  B29K 69/00 (2006.01)
  B29K 1/00 (2006.01)
  B29C 35/16 (2006.01)
  B29C 35/02 (2006.01)
  B29L 31/00 (2006.01)

(52) U.S. Cl.
  CPC ............ *B29C 51/32* (2013.01); *B29C 51/426* (2013.01); *B29C 51/427* (2013.01); *B29C 51/428* (2013.01); *A61M 2037/0023* (2013.01); *A61M 2037/0053* (2013.01); *B29C 35/0261* (2013.01); *B29C 2035/1666* (2013.01); *B29K 2001/00* (2013.01); *B29K 2003/00* (2013.01); *B29K 2023/06* (2013.01); *B29K 2023/12* (2013.01); *B29K 2067/003* (2013.01); *B29K 2067/043* (2013.01); *B29K 2067/046* (2013.01); *B29K 2069/00* (2013.01); *B29K 2077/00* (2013.01); *B29K 2905/00* (2013.01); *B29K 2905/02* (2013.01); *B29K 2905/10* (2013.01); *B29L 2031/7544* (2013.01)

(56) References Cited

U.S. PATENT DOCUMENTS

| | | | | |
|---|---|---|---|---|
| 6,607,513 | B1* | 8/2003 | Down | A61M 37/0015 604/239 |
| 7,131,987 | B2* | 11/2006 | Sherman | A45D 26/0004 604/290 |
| 2007/0004989 | A1* | 1/2007 | Dhillon | A61M 37/0015 600/583 |
| 2012/0004614 | A1* | 1/2012 | Stumber | A01K 11/005 604/173 |
| 2012/0078189 | A1 | 3/2012 | Ogawa et al. | |
| 2014/0052067 | A1 | 2/2014 | Sausse et al. | |
| 2015/0141924 | A1 | 5/2015 | Pricone | |
| 2015/0196746 | A1 | 7/2015 | Ogawa et al. | |
| 2017/0239855 | A1 | 8/2017 | Niitsu et al. | |

FOREIGN PATENT DOCUMENTS

| | | |
|---|---|---|
| JP | 2009-173341 A | 8/2009 |
| JP | 2010-17214 A | 1/2010 |
| JP | 2012-91456 A | 5/2012 |
| JP | 2013-248299 A | 12/2013 |
| JP | 2014-519344 A | 8/2014 |
| JP | 2017-35432 A | 2/2017 |
| JP | 2017-38903 A | 2/2017 |
| JP | 2017-38904 A | 2/2017 |
| WO | WO 2013/170171 A1 | 11/2013 |

\* cited by examiner

MICROPROJECTION IMPLEMENT AND METHOD FOR PRODUCING SAME

TECHNICAL FIELD

The present invention relates to a microprotrusion device that can be used in transdermal absorption of medicaments, and a production method thereof.

BACKGROUND ART

In recent years, in medical fields, cosmetic fields, and the like, attention has been paid to transdermal absorption of medicaments with the use of a liquid injection device that includes fine needle-like protrusions, which are also called microneedles. With this liquid injection device, it is possible to inject a medicament into a human body by introducing the microneedles into a relatively shallow layer of the skin such as the stratum corneum, which significantly reduces pain felt by the subject as compared with an ordinary syringe. Accordingly, attention has been paid to such a liquid injection device as a noninvasive medicament delivery means.

Patent Literature 1 discloses a microneedle device including so-called solid-type microneedles each having a skin-pierceable conical three-dimensional shape and capable of injecting a medicament into a human body by piercing the skin, with the medicament being applied to the surface of the microneedles. The microneedle device disclosed in Patent Literature 1 has a configuration in which a plurality of microneedles having the same shape and dimensions are formed on a substrate surface, the microneedles having a uniform height. Because all of the microneedles pierce the skin when in use, the medicament is applied to the entire surface of each microneedle. The microneedle device according to Patent Literature 1 is produced by heating a substrate made of a thermoplastic resin or the like and pressing the surface of the heated substrate using a mold corresponding to the microneedle arrangement pattern. Accordingly, as is clear from the production method, each microneedle itself has a solid structure.

CITATION LIST

Patent Literature

Patent Literature 1: JP 2013-248299A

SUMMARY OF INVENTION

The present invention relates to a method for producing a microprotrusion device including a needle-like and hollow first protrusion portion that is formed so as to protrude from one surface of a substrate sheet that can be softened by applying heat, and a hollow second protrusion portion that is formed so as to protrude from the vicinity of the first protrusion portion on the one surface of the substrate sheet and has a protrusion height lower than that of the first protrusion portion.

The method according to the present invention includes a first pressing step of, with the use of a first projection mold for forming the first protrusion portion and a heating means for heating an object that is in contact with the first projection mold, abutting a tip end of the first projection mold against the other surface of the substrate sheet and heating the abutment portion, during which the first projection mold is pressed toward the one surface side of the substrate sheet by a predetermined distance so as to deform the pressed portion of the substrate sheet into a shape of the first projection mold.

Also, the method according to the present invention includes a second pressing step of, with the use of a second projection mold for forming the second protrusion portion and a heating means for heating an object that is in contact with the second projection mold, abutting a tip end of the second projection mold against the other surface of the substrate sheet and heating the abutment portion, during which the second projection mold is pressed toward the one surface side of the substrate sheet by a predetermined distance so as to deform the pressed portion of the substrate sheet into a shape of the second projection mold.

A pressed distance of the substrate sheet pressed by the second projection mold is set to be shorter than a pressed distance of the substrate sheet pressed by the first projection mold.

Also, the present invention relates to a microprotrusion device including: a needle-like first protrusion portion that is formed so as to protrude from one surface of a substrate sheet; and a second protrusion portion that is formed so as to protrude from the vicinity of the first protrusion portion on the one surface of the substrate sheet and has a protrusion height lower than that of the first protrusion portion.

DESCRIPTION OF EMBODIMENTS

An advantage of using microneedles in transdermal absorption of medicaments is that, as described above, it is possible to inject a medicament into a relatively shallow layer of the skin such as the stratum corneum and cause less pain felt by the subject than an ordinary syringe. In this regard, if the microneedles have an excessively high protrusion height, the microneedles penetrate too deeply into the skin, and thus such an advantage cannot be obtained. On the other hand, fine microneedles having a low protrusion height are problematic in that it they are difficult to process. For example, in the case of so-called hollow-type microneedles that have a hollow three-dimensional shape and discharge a medicament to the outside through hollow portions, it is not easy to highly accurately form an opening for discharging a medicament, at the tip end of each microneedle during the production process. In order to realize this, the production process may become complex, and the production cost may increase. Accordingly, no technique has been available for producing high-quality microneedles (microprotrusions) that cause less pain even when they penetrate the skin, at a relatively low cost and in a stable manner.

The present invention relates to the provision of a microprotrusion device including microprotrusions, wherein it is possible to control the depth of penetration into the skin and cause less pain when the microprotrusions penetrate the skin. The present invention also relates to the provision of a method for producing a microprotrusion device, with which it is possible to produce the microprotrusion device at a relatively low cost and in a stable manner.

Figure 2A:
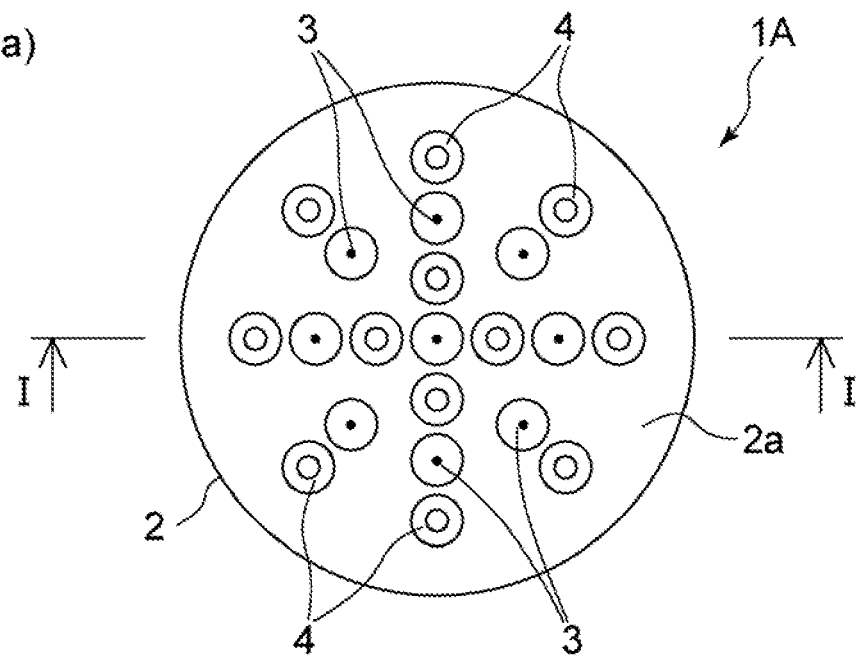
FIG. 2(*a*) is a schematic top view of the microprotrusion device shown in FIG. 1, and FIG. 2(*b*) is a virtual side view showing an arrangement of protrusion portions, taken along the line I-I shown in FIG. 2(*a*).
Figure 2B:
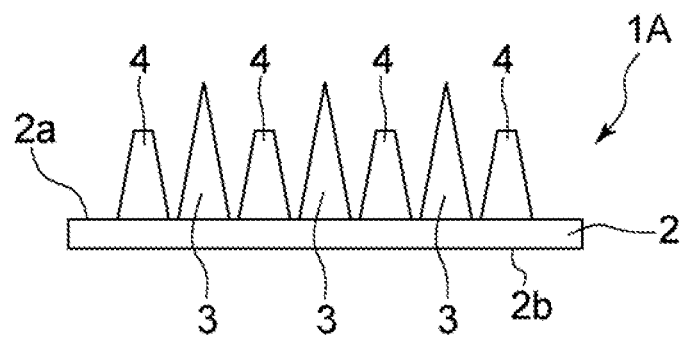
Figure 3:
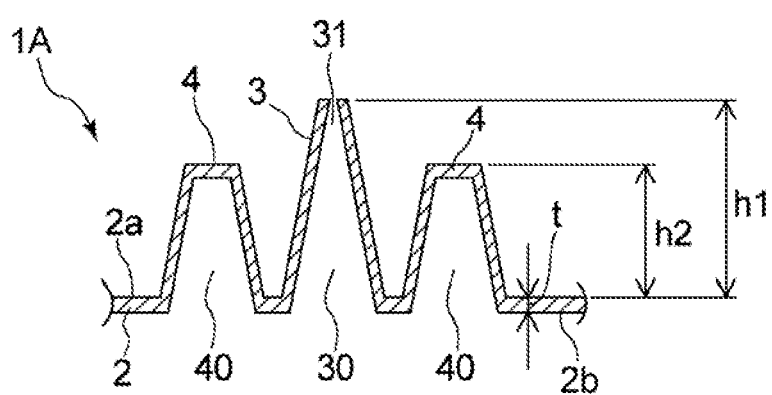
FIG. 3 is a schematic cross-sectional view of a portion of the microprotrusion device shown in FIG. 1, taken along the height direction of the microprotrusion device (the protruding direction of protrusion portions) shown in FIG. 1.

Hereinafter, the present invention will be described with reference to the drawings by way of preferred embodiments. FIGS. 1 to 4 show a microprotrusion device according to an embodiment of the present invention. A microprotrusion device 1A according to the present embodiment includes needle-like and hollow first protrusion portions 3 that are formed so as to protrude from an upper surface 2a that is one surface of a substrate sheet 2 having a circular shape as viewed in plan view, and hollow second protrusion portions 4 that are formed so as to protrude in the vicinity of the first protrusion portions 3 on the upper surface 2a of the substrate sheet 2 and have a lower protrusion height than that of the first protrusion portions 3. As shown in FIG. 3, each of the first protrusion portions 3 is a so-called microneedle, which is a microprotrusion that has a hollow portion 30. Also, in the present embodiment, each of the second protrusion portions 4 is also a microneedle that has a hollow portion 40. As will be described later, the protrusion portions 3 and 4 are formed by pressing projection molds that correspond to the protrusion portions 3 and 4 from the other surface (lower surface) 2b of the substrate sheet 2 toward the one surface (upper surface) 2a so as to deform the pressed portions into the shape of the projection molds, as a result of which, openings are formed in portions of the lower surface 2b of the substrate sheet 2 that correspond to the protrusion portions 3 and 4, and hollow portions 30 and 40 are exposed. In this specification, the term "upper" used in the expression "the upper surface of the substrate sheet" refers to the side of the substrate sheet on which protrusion portions are formed, and the term "lower" used in the expression "the lower surface of the substrate sheet" refers to the side of the substrate sheet on which openings are formed.

Figure 1:
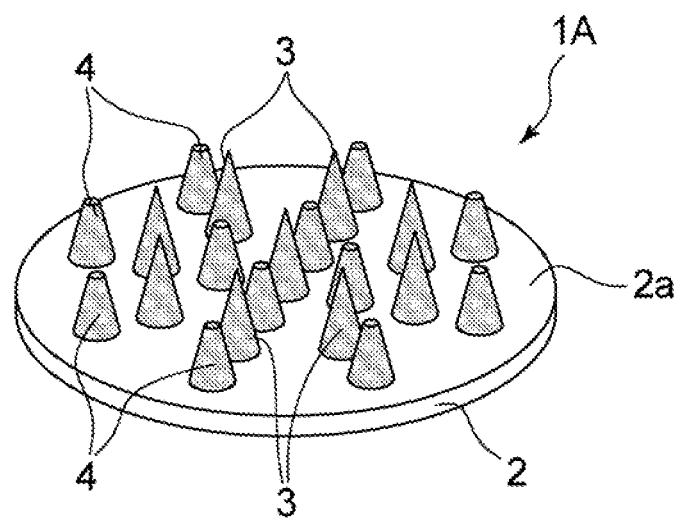
FIG. 1 is a perspective view schematically showing a microprotrusion device according to an embodiment of the present invention.

In the microprotrusion device 1A, as shown in FIGS. 1 and 2, a plurality of first protrusion portions 3 and a plurality of second protrusion portions 4 are formed such that at least one second protrusion portion 4 is formed in the vicinity of a single first protrusion portion 3, more specifically, in a region within 5 mm from a single first protrusion portion 3 in the planar direction. Also, in the microprotrusion device 1A, each first protrusion portion 3 has a circular cone shape, and each second protrusion portion 4 has a truncated cone shape. The plurality of first protrusion portions 3 have the same shape and dimensions, and the plurality of second protrusion portions 4 also have the same shape and dimensions.

Figure 4:
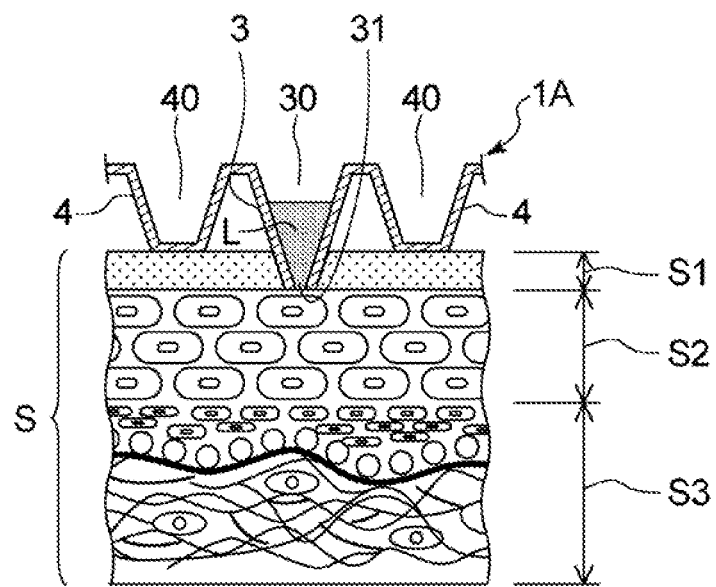
FIG. 4 is a diagram schematically showing the microprotrusion device shown in FIG. 1 when in use, in which a first protrusion portion of the microprotrusion device penetrates into the stratum corneum of the skin, and second protrusion portions are in contact with the skin surface without penetrating the skin.

The microprotrusion device 1A is a liquid injection device that can be used in transdermal absorption of medicaments. For this purpose, in the microprotrusion device 1A, each first protrusion portion 3 has an opening portion 31. More specifically, as shown in FIG. 3, an opening portion 31 is formed at the tip end portion of each first protrusion portion 3, and a hollow portion 30 of the first protrusion portion 3 is in communication with the outside via the opening portion 31. The opening portion 31 is a through hole that extends in the thickness direction through the substrate sheet 2 where first protrusion portions 3 are formed, and is located at the tip end of the circular cone-shaped first protrusion portion 3. The hollow portion 30 of the first protrusion portion 3 functions as a reservoir in which a liquid to be discharged from the opening portion 31 to the outside is stored or a passage through which the liquid to be discharged from the opening portion 31 to the outside passes. In the case where the microprotrusion device 1A is used in transdermal absorption of medicaments, for example, as shown in FIG. 4, the tip end portion of a first protrusion portion 3 penetrates the skin S, and a liquid medicament L stored in the hollow portion 30 of the first protrusion portion 3 is injected into the skin S through the opening portion 31 formed at the tip end portion of the first protrusion portion 3. As described above, the hollow portion 30 of the first protrusion portion 3 functions as a medicament reservoir typically in the case where a medicament is not externally supplied. In the case where a medicament is externally supplied, for example, when a medicament supplier (not shown) such as an applicator is used in combination with the microprotrusion device 1A, the hollow portion 30 functions as a passage through which the medicament passes.

A primary feature of the microprotrusion device 1A is that two different types of protrusion portions 3 and 4 having different protrusion heights protruding from the upper surface 2a of the substrate sheet 2 are provided in close proximity to each other. That is, in the microprotrusion device 1A, one or more second protrusion portions 4 having a relatively low protrusion height are disposed in the vicinity of a first protrusion portion 3 having a relatively high protrusion height (within 5 mm from the first protrusion portion 3 in the planar direction). With this characteristic arrangement of the protrusion portions 3 and 4, the skin penetration depth of the first protrusion portions 3 can be controlled. With this arrangement in which in the vicinity of a first protrusion portion 3 for penetrating the skin, a second protrusion portion 4 having a protrusion height lower than that of the first protrusion portion 3 is provided, and when the first protrusion portion 3 penetrates the skin from its tip end side, the penetration by the first protrusion portion 3 stops when the tip end of the second protrusion portion 4 provided in the vicinity of the first protrusion portion 3 comes into contact with the skin surface (see FIG. 4), which prevents the first protrusion portion 3 from penetrating to a deeper level of the skin. That is, among the two types of protrusion portions 3 and 4 having different protrusion heights in the microprotrusion device 1A, only the first protrusion portion 3 functions as a medicament injection portion by penetrating the skin, and the second protrusion portion 4 having a protrusion height lower than that of the first protrusion portion 3 functions as a stopper that limits the penetration depth of the first protrusion portion 3.

As described above, the microprotrusion device 1A is configured such that the skin penetration depth of the first protrusion portions 3 can be controlled, and it is therefore possible to enable transdermal administration of a medicament to an arbitrary depth of the skin. Accordingly, with the microprotrusion device 1A, it is possible to provide the effect of medicament to the maximum extent possible by adjusting the penetration depth of the first protrusion portions 3 according to the type of medicament or the like. Also, for example, as shown in FIG. 4, the first protrusion portion 3 penetrates into the stratum corneum S1 that is a surface layer portion of the skin S, but does not penetrate into the epidermis S2 and dermis S3 that are deeper levels of the skin S. By doing so, it is possible to significantly reduce the pain associated with transdermal absorption as compared to the use of a conventional syringe. When transdermal absorption of a medicament is performed with the use of a conventional syringe that has an injection needle, it is often the case that the injection needle penetrates beyond the stratum corneum S1 and into the epidermis S2 and the dermis S3, or further into the sub-dermal tissue (not shown) that is deeper than the dermis S3, forcing the subject to withstand the pain associated with the penetration of the injection needle. However, with the microprotrusion device 1A, it is possible to perform transdermal absorption of a medicament without causing the subject to feel pain. The penetration depth of the first protrusion portion 3 matches the protrusion height difference between the first protrusion portion 3 and the second protrusion portion 4 provided in the vicinity of the first protrusion portion 3. Accordingly, the above-described effect can be more reliably obtained by adjusting the protrusion height difference as appropriate.

Referring back to FIG. 3 in which the protrusion height of the first protrusion portion 3 from one surface (upper surface) 2a of the substrate sheet 2 is represented by h1, the protrusion height of each second protrusion portion 4 from the one surface 2a that is provided in the vicinity of the first protrusion portion 3 is represented by h2, and the substantial thickness of the substrate sheet 2 is represented by t, by using the above-described configuration in which "one or more second protrusion portions 4 having a relatively low protrusion height are disposed in the vicinity of a first protrusion portion 3 having a relatively high protrusion height", it is possible to adjust the protrusion heights of the protrusion portions 3 and 4 so as to satisfy the following relationship: h1−h2<t. Since the term "h1−h2" corresponds to the penetration depth of the first protrusion portion 3, the fact that the relationship: h1−h2<t is satisfied indicates that the skin penetration depth of the first protrusion portion 3 can be made smaller than the substantial thickness t of the substrate sheet 2. Such a penetration depth is so minute that it causes little pain when the first protrusion portion 3 penetrates the skin, as long as the substantial thickness t is a normal thickness and is not very thick.

As will be described later, the protrusion portions 3 and 4 are formed by pressing projection molds into the substrate sheet 2 so as to deform the substrate sheet 2. The first protrusion portions 3 each with an opening portion 31 at its tip end portion are formed by, when the projection molds are pressed into the substrate sheet 2, causing the tip ends of the projection molds to pierce through the substrate sheet 2, thereby forming opening portions 31. In this regard, in an aspect in which no second protrusion portions 4 are present and only first protrusion portions 3 are present on the one surface 2a of the substrate sheet 2, in order to shorten the skin penetration depth of the first protrusion portions 3 from the viewpoint of reducing the pain associated with the penetration by the first protrusion portions 3 or the like, if the protrusion height h1 of the first protrusion portions 3 is reduced to be shorter than the substantial thickness t of the substrate sheet 2 (h1<t), the pressed distance of the substrate sheet 2 pressed by the projection molds will be very short as long as the substantial thickness t of the substrate sheet 2 is a normal thickness and is not very thick, and it is therefore difficult for the tip ends of the projection molds to penetrate through the substrate sheet 2, making it difficult to form opening portions 31. In contrast, with the microprotrusion device 1A, the protrusion height difference between two types of protrusion portions 3 and 4 that are in close proximity to each other is the penetration depth, and thus the protrusion height itself of the first protrusion portions 3 can be set to any height irrespective of the substantial thickness t of the substrate sheet 2, and the protrusion height is not necessarily set to be shorter than the substantial thickness t. That is, by using the above-described configuration in which "one or more second protrusion portions 4 having a relatively low protrusion height are disposed in the vicinity of a first protrusion portion 3 having a relatively high protrusion height", it is possible to stably form the first protrusion portions 3 that each have an opening portion 31 for injecting a medicament at its tip end and cause little pain when the first protrusion portions 3 penetrate the skin. In this specification, the expression "the pressed distance of the substrate sheet" refers to the distance by which the projection molds are pressed with reference to the lower surface (the side opposite to the side on which protrusion portions are formed) of the substrate sheet. Accordingly, the pressed distance of the substrate sheet pressed by first projection molds is equal to the total value of the substantial thickness t of the substrate sheet and the height h1 of the first protrusion portions 3, and the pressed distance of the substrate sheet pressed by second projection molds is the total value of the substantial thickness t of the substrate sheet and the height h2 of the second protrusion portion 4.

There is no particular limitation on the protrusion heights of the protrusion portions 3 and 4, and the protrusion heights of the protrusion portions 3 and 4 can be adjusted as appropriate according to the application of the microprotrusion device 1A, or the like. However, from the viewpoint of achieving micro-sized needles suitable to be referred to as so-called microneedles (microprotrusions) and that enable penetration from the stratum corneum to a depth corresponding to the dermis of a human, it is preferable to set the protrusion height of the protrusion portions 3 and 4 as follows.

The protrusion height h1 of the first protrusion portions 3 is preferably 0.01 mm or more, more preferably 0.02 mm or more, and preferably 10 mm or less, and more preferably 5 mm or less. More specifically, the protrusion height h1 of the first protrusion portions 3 is preferably 0.01 mm or more and 10 mm or less, and more preferably 0.02 mm or more and 5 mm or less.

The protrusion height h2 of the second protrusion portions 4 is preferably 0.02 mm or more, more preferably 0.03 mm or more, and preferably 5 mm or less, and more preferably 4 mm or less. More specifically, the protrusion height h2 of the second protrusion portions 4 is preferably 0.02 mm or more and 5 mm or less, and more preferably 0.03 mm or more and 4 mm or less.

The protrusion height difference h1−h2 between the protrusion portions 3 and 4 is preferably 0.001 mm or more, more preferably 0.005 mm or more, and preferably 5 mm or less, and more preferably 4 mm or less. More specifically, the protrusion height difference h1−h2 between the protrusion portions 3 and 4 is preferably 0.001 mm or more and 5 mm or less, and more preferably 0.005 mm or more and 4 mm or less.

The substantial thickness t of the substrate sheet 2 is preferably 0.005 mm or more, more preferably 0.01 mm or more, and preferably 1.0 mm or less, and more preferably 0.5 mm or less. More specifically, the substantial thickness t of the substrate sheet 2 is preferably 0.005 mm or more and 1.0 mm or less, and more preferably 0.01 mm or more and 0.5 mm or less.

The tip end diameter of the first protrusion portions 3 is preferably 0.001 mm or more, more preferably 0.005 mm or more, and preferably 0.5 mm or less, and more preferably 0.3 mm or less. More specifically, the tip end diameter of the first protrusion portions 3 is preferably 0.001 mm or more and 0.5 mm or less, and more preferably 0.005 mm or more and 0.3 mm or less.

The tip end diameter of the second protrusion portions 4 is preferably 0.002 mm or more, more preferably 0.01 mm or more, and preferably 5 mm or less, and more preferably 2 mm or less. More specifically, the tip end diameter of the second protrusion portions 4 is preferably 0.002 mm or more and 5 mm or less, and more preferably 0.01 mm or more and 2 mm or less.

The tip end diameters of the protrusion portions 3 and 4 are measured using the following method.

Figure 5:
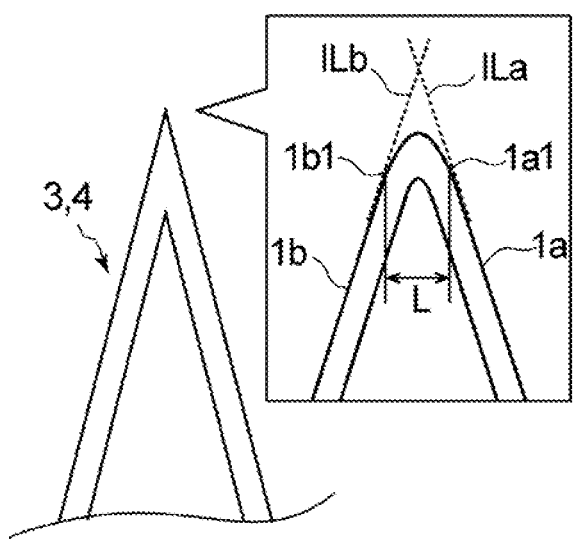
FIG. 5 is an illustrative diagram showing a method for measuring the tip end diameter of a protrusion portion of the microprotrusion device.

Method for Measuring Tip End Diameter of Protrusion Portions of Microprotrusion Device The tip end portion of a protrusion portion (first protrusion portion 3 or second protrusion portion 4) that is a measurement target is observed by using a scanning electron microscope (SEM) or a microscope as shown in an SEM image in FIG. 5. Next, as shown in FIG. 5, an imaginary line Ila is drawn so as to extend along a straight line portion of one side 1a that is one of two sides 1a and 1b, and an imaginary line ILb is drawn so as to extend along a straight line portion of the other side 1b. Then, on the tip end side, the point where the one side 1a is separated from the imaginary line Ila is determined as a first tip end point 1a1, and the point where the other side 1b is separated from the imaginary line ILb is determined as a second tip end point 1b1. Length L of a straight line connecting the first tip end point 1a1 and the second tip end point 1b1 determined above is measured by using a scanning electron microscope (SEM), and the measured length of the straight line is defined as the tip end diameter of the protrusion portion that is a measurement target.

As described above, in the microprotrusion device 1A, the second protrusion portions 4 function as stoppers that limit the penetration depth of the first protrusion portions 3, and thus are not designed to penetrate the skin. For this reason, each second protrusion portion 4 is not open and does not have an opening portion on the upper surface 2a side of the substrate sheet 2.

Also, the second protrusion portion 4 functions as a stopper due to its tip end abutting against the skin surface. Accordingly, the tip end of the second protrusion portion 4 preferably has a shape that causes less pain even when it comes into abutment against the skin. From this viewpoint, as viewed in side view shown in FIG. 2(b), the tip ends of the second protrusion portions 4 preferably have a horizontally extending straight line or a curve projecting in the protruding direction of the second protrusion portions 4 (the penetration direction of the first protrusion portions 3). As shown in FIGS. 1 to 4, the tip ends of the second protrusion portions 4 of the microprotrusion device 1A have a straight line as viewed in side view. That is, the tip ends of the second protrusion portions 4 have a flat surface without depressions or projections.

In order to more reliably cause the second protrusion portions 4 to exhibit the function of limiting the penetration depth of the first protrusion portions 3, it is necessary to think out the arrangement of the protrusion portions 3 and 4. From this viewpoint, as shown in FIG. 2(a), the microprotrusion device 1A includes "an area that is in the vicinity of a single first protrusion portion 3 (within 5 mm from the single first protrusion portion 3 in the planar direction) and in which at least a pair of second protrusion portions 4 are provided at opposing positions with the single first protrusion portion 3 interposed therebetween" (hereinafter also referred to as a specific protrusion portion arrangement area). In FIG. 2(a), in each of a vertical linear array that is composed of protrusion portions 3 and 4 and extends in the up down direction in FIG. 2(a) through a single first protrusion 3 that has a circular shape as viewed from above and is located at the center of the substrate sheet 2 and a horizontal linear array that is composed of protrusion portions 3 and 4 and extends in the right left direction in FIG. 2(a) through the single first protrusion 3, specific protrusion portion arrangement areas as described above are continuously present in the linear array directions. In each of the specific protrusion portion arrangement areas, the second protrusion portions 4 that function as stoppers that limit the penetration depth of the first protrusion portions 3 are disposed on two sides of the single first protrusion 3. Accordingly, with the microprotrusion device 1A including such a specific protrusion portion arrangement area, the penetration depth of the first protrusion portions 3 is more reliably limited, and thus the disadvantage of unintentional deep penetration by the first protrusion portions 3 is unlikely to occur.

The arrangement of the protrusion portions 3 and 4 in the microprotrusion device 1A will be described in further detail. When the microprotrusion device 1A is viewed from above as shown in FIG. 2(a), around a single first protrusion 3, a plurality of other first protrusion portions 3 and a plurality of second protrusion portions 4 are disposed radially, and in at least one (the vertical linear array and the horizontal linear array) of the plurality of radial directions, first protrusion portions 3 and second protrusion portions 4 are alternately provided, and a plurality of protrusion portions 3 and 4 are arranged in a radial pattern. The single first protrusion 3 at the center of the radial pattern is located at the center of the substrate sheet 2 that has a circular shape as viewed in plan view.

FIGS. 6(a) to 9(b) show microprotrusion devices according to other embodiments of the present invention and relevant parts thereof. The other embodiments given below will be described focusing on constituent elements that are different from those of the embodiment described above. The constituent elements that are the same as those of the above-described embodiment will be given the same reference numerals, and a description thereof will be omitted. The constituent elements that are not described specifically are the same as those of the microprotrusion device 1A according to the embodiment given above.

Figure 6A:
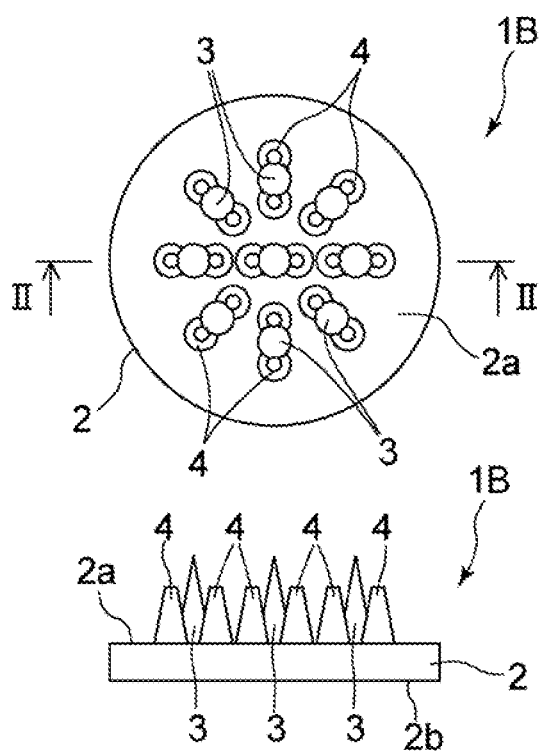
FIG. 6(*a*) is a schematic top view of a microprotrusion device according to another embodiment of the present invention (corresponding to FIG. 2(*a*)), and FIG. 6(*b*) is a virtual side view showing an arrangement of protrusion portions, taken along the line II-II shown in FIG. 6(*a*).
Figure 6B:
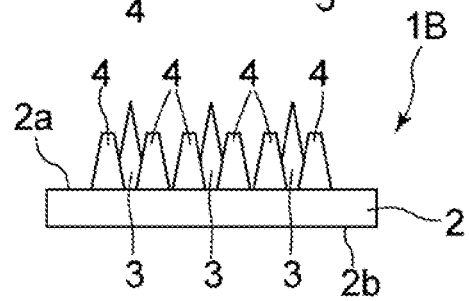

In a microprotrusion device 1B shown in FIG. 6, a single first protrusion 3 and second protrusion portions 4 that are disposed in the vicinity of the single first protrusion 3 are connected at their root portions (the end portions opposite to the tip end portions of the protrusion portions in the protruding direction). More specifically, as shown in FIG. 6(a), a plurality of protrusion portions 3 and 4 are arranged in a radial pattern on the upper surface 2a of the substrate sheet 2, and all of the plurality of protrusion portions 3 and 4 constitute specific protrusion portion arrangement areas as described above. Specifically, there are nine specific protrusion portion arrangement areas on the upper surface 2a. As shown in FIG. 6(b), in each of the nine specific protrusion portion arrangement areas, a single first protrusion 3 and two second protrusion portions 4 and 4 that are disposed opposing each other with the single first protrusion 3 interposed therebetween are formed into a unit by being connected only at their root portions, and the tip end portions of the protrusion portions 3 and 4 are independently present without being connected. As used herein, the expression "connected at their root portions" refers to a state in which the single first protrusion portion 3 and two second protrusion portions 4 are continuous on one surface of the substrate sheet 2, or in other words, at a position on the tip end side of the protrusion portions 3 and 4 in the protruding direction thereof relative to the upper surface 2a that forms as a base height. In the present embodiment, "connected root portion" of the protrusion portions 3 and 4 that constitute a specific protrusion portion arrangement area as described above serves as a valley portion between the protrusion portions 3 and 4.

Figure 7A:
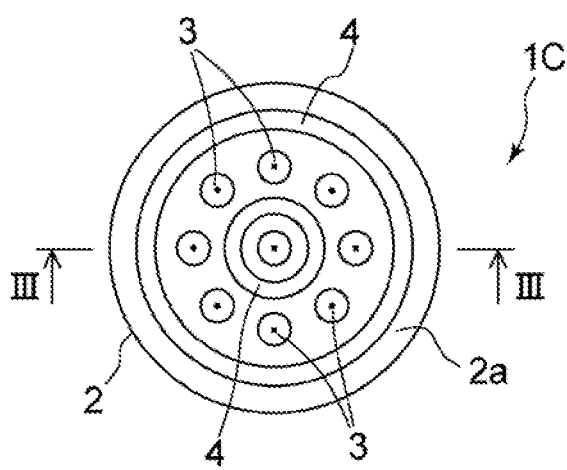
FIG. 7(*a*) is a schematic top view of a microprotrusion device according to still another embodiment of the present invention, and FIG. 7(*b*) is a virtual side view showing an arrangement of protrusion portions, taken along the line III-III shown in FIG. 7(*a*).
Figure 7B:
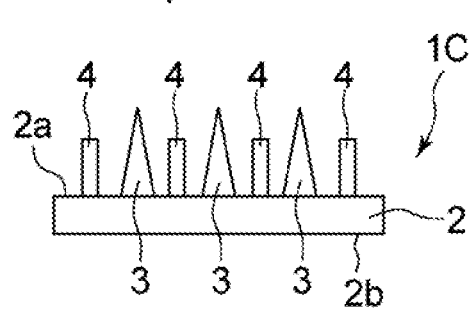

In a microprotrusion device 1C shown in FIG. 7, the second protrusion portions 4 have a continuous annular shape as viewed from above. More specifically, as shown in FIG. 7(a), a second protrusion portion 4 having an annular shape as viewed in plan view is provided so as to surround a single first protrusion 3 located at the center of the substrate sheet 2 that has a circular shape as viewed in plan view. Furthermore, a plurality of (eight) first protrusion portions 3 are provided along the second protrusion portion 4 on the outside of the annular-shaped second protrusion portion 4 the microprotrusion device 1C so as to surround the second protrusion portion 4. Furthermore, another second protrusion portion 4 having an annular shape as viewed in plan view is provided so as to surround the plurality of first protrusion portions 3. The two annular-shaped second protrusion portions 4 and 4 are concentrically arranged.

Figure 8A:
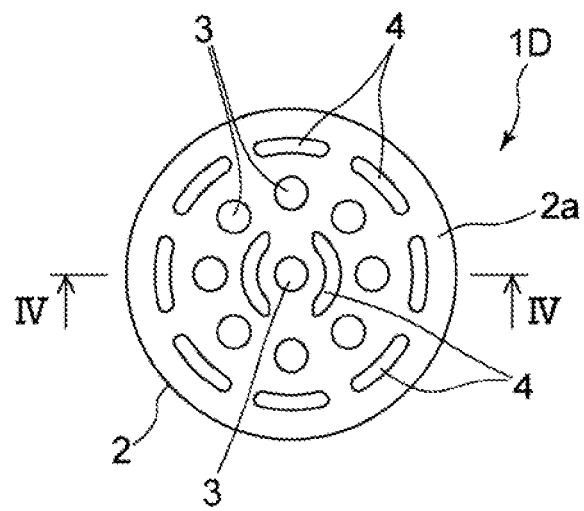
FIG. 8(*a*) is a schematic top view of a microprotrusion device according to still another embodiment of the present invention, and FIG. 8(*b*) is a virtual side view showing an arrangement of protrusion portions, taken along the line IV-IV shown in FIG. 8(*a*).
Figure 8B:
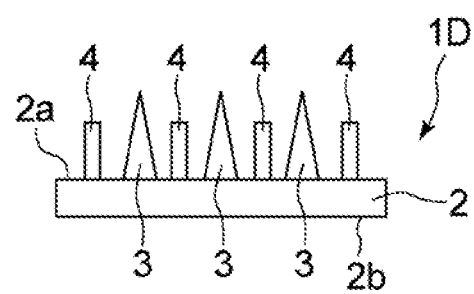

A microprotrusion device 1D shown in FIG. 8 has the same configuration as that of the microprotrusion device 1C shown in FIG. 7, except that each second protrusion portion 4 has a discontinuous annular shape as viewed from above, and a plurality of protrusion portions 3 and 4 are arranged in a radial pattern on the upper surface 2a of the substrate sheet 2. That is, as shown in FIG. 8(a), the second protrusion portions 4 of the microprotrusion device 1D are in the shape of an arc as viewed from above.

Figure 9A:
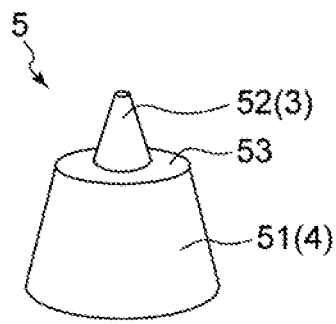
FIG. 9(*a*) is a perspective view of a protrusion portion according to another embodiment of the present invention, and FIG. 9(*b*) is a schematic cross-sectional view of the protrusion portion shown in FIG. 9(*a*), taken at an arbitrary position along the height direction of the protrusion portion (the protruding direction of the protrusion portion) shown in FIG. 9(a).
Figure 9B:
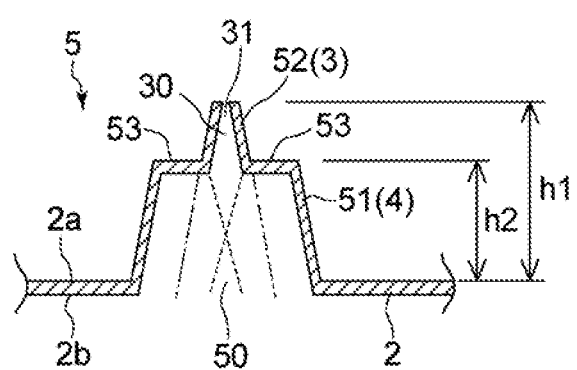

In the microprotrusion device 1B shown in FIG. 6, a single first protrusion 3 and second protrusion portions 4 disposed in the vicinity of the single first protrusion 3 that constitute a specific protrusion portion arrangement area as described above are connected only at their root portions, but as in a specific protrusion portion 5 shown in FIG. 9, a second protrusion portion 4 may be connected to a first protrusion portion 3 that is disposed in the vicinity of the second protrusion portion 4 not only at its root portion but also at its tip end portion. The specific protrusion portion 5 is a protrusion portion in which second protrusion portions 4 are connected to a first protrusion portion 3 that is disposed in the vicinity of the second protrusion portions 4, at their tip end portion and root portion. As shown in FIG. 9, the specific protrusion portion 5 includes a root portion 51 that extends upward from the upper surface 2a of the substrate sheet 2, and a tip end portion 52 that is joined to the tip end of the root portion 51 in the protruding direction of the root portion 51. The tip end portion 52 is surrounded by a flat portion 53 that is parallel to the upper surface 2a, and is located at the central portion of the flat portion 53. The root portion 51 is composed of second protrusion portions 4, and the tip end portion 52 is composed of a first protrusion portion 3. The flat portion 53 is composed of tip ends of the second protrusion portions 4 in the protruding direction thereof, and has a linear shape extending in the horizontal direction as viewed in cross section as shown in FIG. 9(b). The specific protrusion portion 5 shown in FIG. 9 has a non-directional shape as viewed in plan view (as viewed from above), and has a cross section as shown in FIG. 9(b), the cross section being taken along the height direction of the specific protrusion portion 5 (the protruding direction of the specific protrusion portion 5) at an arbitrary position. Dash dot lines shown in FIG. 9(b) are contour lines of virtual side surfaces of the single first protrusion 3 that constitutes the specific protrusion portion 5, and dotted lines shown in FIG. 9(b) are contour lines of virtual side surfaces of two second protrusion portions 4 and 4 that constitute the specific protrusion portion 5. Accordingly, these lines are contour lines that do not actually exist. A hollow portion 50 of the specific protrusion portion 5 forms one continuous unpartitioned space portion, and is in communication with the outside via an opening portion 31 formed at the tip end.

When the tip end portion 52 (the tip end portion of the first protrusion portion 3) of the specific protrusion portion 5 penetrates the skin, the flat portion 53 (the tip end of the second protrusion portion 4) located at the root of the tip end portion 52 functions as a stopper that limits the penetration of the tip end portion 52. Also, the hollow portion 50 of the specific protrusion portion 5 has a shape as shown in FIG. 9(b) in which an isosceles triangle is joined at a central portion of the upper base of an isosceles trapezoid as viewed in cross section taken along the protruding direction (the height direction of the microprotrusion device) of the specific protrusion portion 5. Accordingly, when the isosceles triangle shaped portion, or in other words, the tip end portion 52 penetrates the skin, the liquid stored in the hollow portion 50 flows concentratedly into the tip end portion 52, as a result of which, all of the liquid can be discharged from the opening portion 31, and thus a disadvantage of the liquid remaining in the hollow portion 50 is unlikely to occur.

Figure 10:
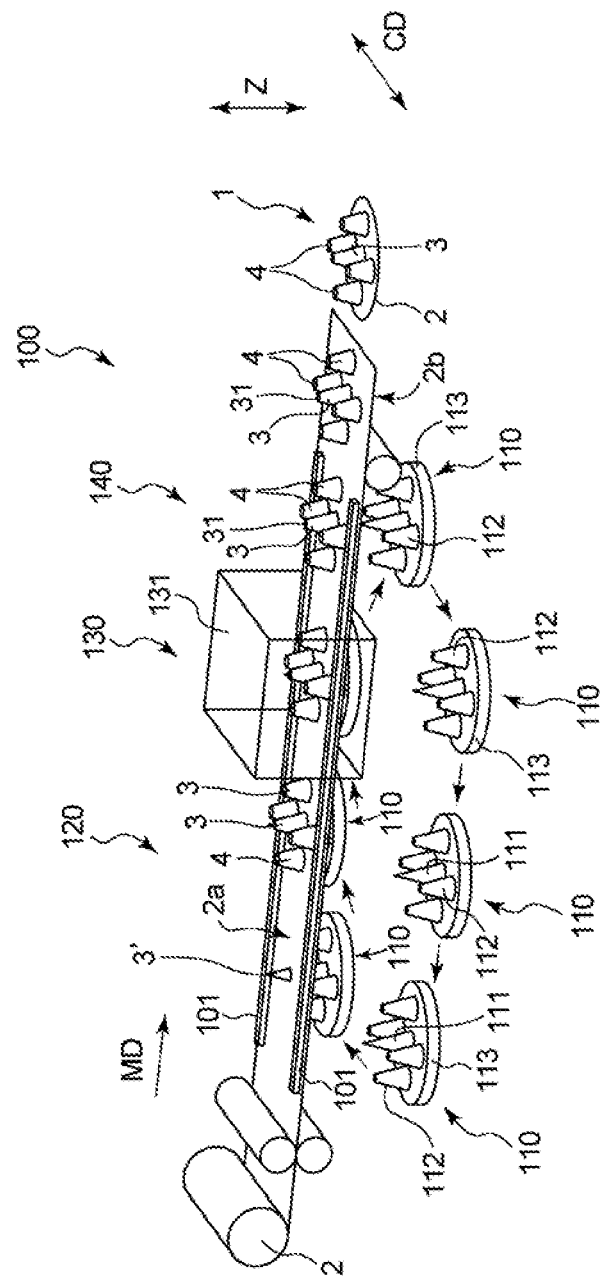
FIG. 10 is a diagram showing an overall configuration of a production apparatus used to carry out a method for producing a microprotrusion device according to an embodiment of the present invention.

Next, a method for producing a microprotrusion device according to the present invention will be described by way of a preferred embodiment with reference to the drawings. FIG. 10 shows a production apparatus used to carry out a method for producing a microprotrusion device according to an embodiment of the present invention. A production apparatus 100 according to the present embodiment is a production apparatus for producing a microprotrusion device 1 including all of the features of the microprotrusion device 1A described above. The microprotrusion device 1 is a compact version of the microprotrusion device 1 obtained by miniaturizing the substrate sheet 2 and reducing the number of protrusion portions 3 and 4. Note that in FIG. 10, from the viewpoint of ease of understanding, microprotrusion devices 1A are illustrated in a scale greater than their actual size.

As shown in FIG. 10, the production apparatus 100 is configured such that an elongated strip-shaped substrate sheet 2 wound into a roll is unwound and conveyed in one direction, and first projection molds 111 and second projection molds 112 are pressed into the conveyed substrate sheet 2 from one surface side of the substrate sheet 2 to the other surface side so as to deform the substrate sheet 2 and form first protrusion portions 3 corresponding to the first projection molds 111 and second protrusion portions 4 corresponding to the second projection molds 112. The production apparatus 100 includes, from the upstream side to the downstream side in the conveyance direction of the substrate sheet 2, a protrusion portion forming unit 120, a cooling unit 130, and a release unit 140. In the diagram, the reference character MD (Machine Direction) indicates the conveyance direction of the substrate sheet 2 (the lengthwise direction of the substrate sheet 2), the reference character CD (Cross machine Direction) indicates a direction perpendicular to the conveyance direction (the width direction of the substrate sheet 2), and the reference character Z indicates the thickness direction of the substrate sheet 2.

The substrate sheet 2 is a sheet that can be softened by applying heat, and the deformation of the substrate sheet 2 (the formation of protrusion portions 3 and 4) by pressing the projection molds 111 and 112 is implemented through the application of heat so as to soften and melt abutment portions of the substrate sheet 2 that are in abutment with the projection molds 111 and 112. As the substrate sheet 2, a sheet containing a thermoplastic resin can be used. Examples of the thermoplastic resin include poly-fatty acid ester, polycarbonate, polypropylene, polyethylene, polyester, polyamide, polyamide imide, polyether ether ketone, polyether imide, polystyrene, polyethylene terephthalates, poly(vinyl chloride), nylon resin, acrylic resin, and the like. These thermoplastic resins may be used singly or in a combination of two or more. Among the thermoplastic resins, from the viewpoint of biodegradability, it is preferable to use a poly-fatty acid ester. Specifically, polylactic acid, polyglycolic acid, a combination thereof, and the like can be used. The substrate sheet 2 may be made of, instead of the thermoplastic resin, a mixture containing hyaluronic acid, collagen, starch, cellulose, and the like.

In the production apparatus 100, from the viewpoint of more reliably deforming the substrate sheet 2 by pressing the projection molds 111 and 112 into the substrate sheet 2, as shown in FIG. 10, opposite side edge portions of the conveyed substrate sheet 2 extending along the MD direction are supported by a pair of supporting members 101 and 101. The pair of supporting members 101 and 101 extend continuously spanning the protrusion portion forming unit 120, the cooling unit 130 and the release unit 140, and are provided on the upper surface 2a side of the substrate sheet 2, or in other words, on the opposite side from which the projection molds 111 and 112 are pressed. When the projection molds 111 and 112 are pressed against a portion of the substrate sheet 2 that is between the supporting members 101 and 101 from the lower surface 2b side of the substrate sheet 2 toward the upper surface 2a side, with the opposite side edge portions of the substrate sheet 2 being supported by the pair of supporting members 101 and 101, a problem in which the substrate sheet 2 cannot withstand the pressing force and comes loose will not occur, and it is therefore possible to form the protrusion portions 3 and 4 in a more stable manner.

In the production method according to the present embodiment, pressing tools 110 integrated with the first projection molds 111 and the second projection molds 112 are used. As shown in FIG. 10, a pressing tool 110 includes, on one surface (upper surface) of a substrate 113, a first projection mold 111 for forming a first protrusion portion 3 and second projection molds 112 for forming second protrusion portions 4. As described above, because the first protrusion portion 3 and the second protrusion portions 4 have different protrusion heights, the second projection molds 112 have a protrusion height from the substrate 113 lower than that of the first projection mold 111. The pressing tool 110 has a shape representing the shape of the microprotrusion device 1 that is the intended product, and the shape and arrangement of the projection molds 111 and 112 are substantially the same as those of the microprotrusion device 1. The first projection mold 111 has an acute tip end so as to be capable of easily piercing through the substrate sheet 2, but the second projection molds 112 have a flat obtuse tip end so as to be unlikely to pierce through the substrate sheet 2.

The pressing tool 110 includes a heating means (not shown) that heats an object (substrate sheet 2) that is in contact with the projection molds 111 and 112. By bringing the projection molds 111 and 112 into abutment against the substrate sheet 2 to be heated and heating the abutment portions with the use of the heating means, the abutment portions can be softened and melted. As the heating means, a heat generating apparatus such as a heater apparatus can be used. It is also possible to use a means (ultrasonic vibrator apparatus) that ultrasonically vibrates the projection molds 111 and 112. By abutting the projection molds 111 and 112 ultrasonically vibrated through the operation of the ultrasonic vibrator apparatus against the substrate sheet 2, it is possible to generate frictional heat in the abutment portions of the substrate sheet 2, and soften and melt the abutment portions. In the present embodiment, as the heating means, an ultrasonic vibrator apparatus is used. The heating means can be provided at any location within or outside the pressing tool 110 such that the heating means can fulfil its function.

The heating temperature when the substrate sheet 2 is heated by the heating means is preferably greater than or equal to the glass transition temperature (Tg) of the substrate sheet 2, and more preferably greater than or equal to the softening temperature of the substrate sheet 2. Also, the heating temperature is preferably less than the melting point of the substrate sheet 2.

As used herein, the term "glass transition temperature (Tg) of the substrate sheet" means the glass transition temperature Tg of the resin that constitutes the substrate sheet. In the case where there are a plurality of constituent resins, and they have different glass transition temperatures Tg, the heating temperature of the substrate sheet heated by the heating means is preferably at least greater than or equal to the lowest of the glass transition temperatures Tg of the plurality of constituent resins, and more preferably greater than or equal to the highest of the glass transition temperatures Tg of the plurality of constituent resins.

The same applies to the term "the softening temperature of the substrate sheet". That is, in the case where there are a plurality of constituent resins that constitute the substrate sheet, and they have different softening temperatures, the heating temperature of the substrate sheet heated by the heating means is preferably at least greater than or equal to the lowest of the softening temperatures of the plurality of constituent resins, and more preferably greater than or equal to the highest of the softening temperatures of the plurality of constituent resins.

Also, in the case where the substrate sheet is composed of two or more resins having different melting points, the heating temperature of the substrate sheet heated by the heating means is preferably less than the lowest of the melting points of the two or more resins.

The aforementioned "glass transition temperature Tg of the substrate sheet" is measured by using the following method, and the aforementioned "the softening temperature of the substrate sheet" is measured in accordance with JIS K-7196: Testing Method for Softening Temperature of Thermoplastic Film and Sheet by Thermomechanical Analysis.

Method for Measuring Glass Transition Temperature (Tg) of Substrate Sheet

A differential scanning calorimeter (Diamond DSC) available from Perkin Elmer is used as a measuring instrument. From a substrate sheet that is a measurement target, 10 mg of test piece is taken, and the test piece is heated under a predetermined conditions. Specifically, the test piece is kept at 20° C. for 5 minutes, and thereafter the temperature is increased from 20° C. to 220° C. at a rate of 5° C./min, and a DSC curve is obtained in which the horizontal axis represents temperature and the vertical axis represents the amount of heat. Then, glass transition temperature Tg is determined based on the DSC curve.

The projection molds 111 and 112 are made of a high-strength material that is resistant to breakage. Examples of the material of the projection molds 111 and 112 include: metals such as steel, stainless steel, aluminum, aluminum alloys, nickel, nickel alloys, cobalt, cobalt alloys, copper, copper alloys, beryllium copper, and beryllium copper alloys; ceramic; and the like. The substrate 113 on which the projection molds 111 and 112 are formed can be formed by using the same material as that of the projection molds 111 and 112.

As shown in FIG. 10, the pressing tool 110 is configured to be capable of being conveyed along with the substrate sheet 2 passing the protrusion portion forming unit 120, the cooling unit 130, and the release unit 140, on the lower surface 2b side of the conveyed substrate sheet 2. Also, the pressing tool 110 is configured to be capable of being moved in the thickness direction Z by a piston cylinder (not shown). The operation of pressing the pressing tool 110 into the substrate sheet 2 in the protrusion portion forming unit 120 and the operation of withdrawing the pressing tool 110 in the release unit 140 are carried out by the piston cylinder. The series of operations of the pressing tool 110 (the operations of the piston cylinder and the conveyor) are controlled by a control means (not shown).

The production method according to the present embodiment includes a first pressing step in which the first projection mold 111 and the heating means (ultrasonic vibrator apparatus) are used and a second pressing step in which the second projection molds 112 and the heating means are used. The first pressing step is a step for forming a first protrusion portion 3, and the second pressing step is a step for forming second protrusion portions 4. A primary feature of the production method according to the present embodiment is that the two steps can be carried out simultaneously by using the pressing tool 110.

The production method according to the present invention encompasses an "aspect that includes: a step of carrying out the first pressing step by using a pressing tool (not shown) that includes the first projection mold 111 but does not include the second projection mold 112; and a step of carrying out the second pressing step by using a pressing tool (not shown) that includes the second projection mold 112 but does not include the first projection mold 111, wherein the two pressing steps are carried out in an arbitrary order". In this aspect, the substrate sheet 2 is cooled after each pressing step has been carried out. This aspect requires the same number of pressing steps as the number of a plurality of types of (two different types of) protrusion portions 3 and 4 included in the microprotrusion device 1 that is the intended product to be performed, which may cause problems such as making the production process complex, increasing the production cost, and reducing the processing accuracy. However, with the production method according to the present embodiment that uses the production apparatus 100, the first and second pressing steps can be carried out simultaneously with a single pressing operation of the pressing tool 110 that is integrated with the projection molds 111 and 112. Accordingly, it is only necessary to perform a relatively small number of steps, and it is therefore possible to produce the microprotrusion device at a relatively low cost with high accuracy in a stable manner.

In the production apparatus 100, first, in the protrusion portion forming unit 120, the tip end of the first projection mold 111 is abutted against the lower surface (the other surface) 2b of the substrate sheet 2 and the abutment portion is heated by the heating means (ultrasonic vibrator apparatus), during which the first projection mold 111 is pressed toward the upper surface (one surface) 2a of the substrate sheet 2 by a predetermined distance so as to deform the pressed portion of the substrate sheet 2 into a shape of the first projection mold 111 (first pressing step), and at the same time, the tip ends of the second projection molds 112 are abutted against the lower surface 2b of the substrate sheet 2 and the abutment portion is heated by the heating means (ultrasonic vibrator apparatus), during which the second projection mold 112 is pressed toward the upper surface 2a of the substrate sheet 2 by a predetermined distance so as to deform the pressed portions of the substrate sheet 2 into a shape of the second projection molds 112 (second pressing step). The first protrusion portion 3 is formed by performing pressing using the first projection mold 111, and the second protrusion portions 4 are formed by performing pressing using the second projection molds 112. As described above, the second protrusion portions 4 have a protrusion height from the upper surface 2a of the substrate sheet 2 lower than that of the first protrusion portion 3. Accordingly, the pressed distance of the substrate sheet pressed 2 by the second projection molds 112 is correspondingly shorter than the pressed distance of the substrate sheet 2 pressed by the first projection mold 111.

Figure 11A:
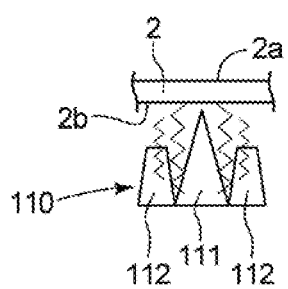
FIGS. 11(a) to 11(e) are illustrative diagrams showing principal steps of the method for producing a microprotrusion device performed by using the production apparatus shown in FIG. 10.

In the protrusion portion forming unit 120, as described above, the first and second pressing steps are carried out simultaneously by using the pressing tool 110. That is, as shown in FIG. 11(a), in a state in which the tip ends of the first projection mold 111 and the second projection molds 112 are directed toward the lower surface 2b of the substrate sheet 2, and the heating means (ultrasonic vibrator apparatus) is running, as shown in FIGS. 11(b) and 11(c), the pressing tool 110 is pressed from the lower surface 2b side of the substrate sheet 2 toward the upper surface 2a side, and the first and second pressing steps are carried out simultaneously with a single pressing operation of the pressing tool 110.

In the pressing operation of the pressing tool 110, the ultrasonically vibrated acute tip end of the first projection mold 111 having a relatively high protrusion height first pierces into the lower surface 2b of the substrate sheet 2. When the pressing tool 110 is further pressed, the tip end of the first projection mold 111 softens and melts the surrounding resin using frictional heat generated by ultrasonic vibration of the tip end, and at the same time moves the substrate sheet 2 in the thickness direction. Along with the movement of the tip end of the first projection mold 111, the substrate sheet 2 is deformed into a shape of the tip end. As a result, a first protrusion portion precursor 3' is formed in a protruding manner on the upper surface 2a side of the substrate sheet 2. The first protrusion portion precursor 3' is a protrusion portion having a lower protrusion height than that of the first protrusion portion 3, and as a result of the first projection mold 111 present in the hollow portion of the first protrusion portion precursor 3' being further pressed by a predetermined distance, a first protrusion portion 3 is finally formed. On the other hand, the ultrasonically vibrated flat tip ends of the second projection molds 112 having a relatively low protrusion height are abutted against the lower surface 2b of the substrate sheet 2 after the first projection mold 111 has been abutted against the lower surface 2b (see FIG. 11(b)). In the embodiment shown in the diagram, the timing of the tip ends of the second projection molds 112 abutting against the lower surface 2b of the substrate sheet 2 is after the first protrusion portion precursor 3' has been formed, but depending on the protrusion height difference between the projection molds 111 and 112 and the thickness of the substrate sheet 2, the timing may be before the first protrusion portion precursor 3' is formed.

Figure 11B:
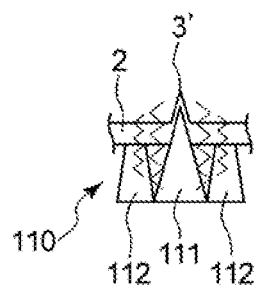

In the state shown in FIG. 11(b), when the pressing tool 110 is further pressed toward the upper surface 2a side of the substrate sheet 2, the first protrusion portion precursor 3' is deformed into a first protrusion portion 3 by the first projection mold 111 being pressed. Also, in the process of forming the first protrusion portion 3, the acute tip end of the first projection mold 111 penetrates through the substrate sheet 2 in the thickness direction, and the penetrated portion serves as an opening portion 31. On the other hand, as shown in FIG. 11(b), in a state in which the tip ends of the second projection molds 112 are abutted against the lower surface 2b of the substrate sheet 2, the tip ends of the second projection molds 112 soften and melt the surrounding resin using frictional heat generated by ultrasonic vibration of the tip ends, and at the same time moves the substrate sheet 2 in the thickness direction. Along with the movement of the tip ends of the second projection molds 112, the substrate sheet 2 is deformed into a shape of the tip ends. As a result, second protrusion portions 4 are formed in a protruding manner on the upper surface 2a side of the substrate sheet 2 (see FIG. 11(c)). The first protrusion portion 3 and the second protrusion portions 4 in the vicinity of the first protrusion portion 3 are formed substantially simultaneously.

Figure 11C:
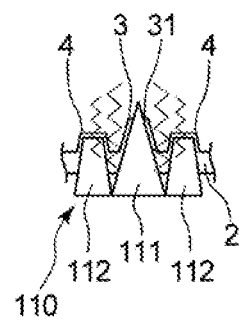
Figure 11D:
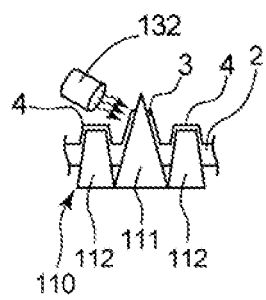

The substrate sheet 2 on which the protrusion portions 3 and 4 have been formed is then, as shown in FIG. 10, transferred to the cooling unit 130 with the corresponding projection molds 111 and 112 being inserted in the protrusion portions 3 and 4 (the state shown in FIG. 11(c)). In the cooling unit 130, the substrate sheet 2 is cooled together with the projection molds 111 and 112. Through the cooling step, the protrusion portions 3 and 4 that were softened through the application of heat are solidified. The cooling unit 130 includes a cold air blowing apparatus 131. The cold air blowing apparatus 131 includes a case body that completely covers an area of the conveyed substrate sheet 2 that corresponds to a microprotrusion device. As shown in FIG. 11(d), the cold air blowing apparatus 131 blows cold air through an air vent 132 from the upper surface 2a side toward the substrate sheet 2 passing through the case body so as to cool the substrate sheet 2 together with the first projection mold 111 and the second projection molds 112 that are inserted into the protrusion portions 3 and 4. The cooling temperature, the cooling time, and the like of the cold air blowing apparatus 131 are controlled by a control means (not shown). If the projection molds 111 and 112 inserted in the protrusion portions 3 and 4 are ultrasonically vibrated while the substrate sheet 2 is still cooling and solidifying, an error may occur in the shape and dimensions of the protrusion portions 3 and 4. For this reason, it is preferable that the projection molds 111 and 112 are ultrasonically vibrated only in the protrusion portion forming unit 120, and the projection molds 111 and 112 are not ultrasonically vibrated in the cooling step.

After the cooling step in the cooling unit 130, as shown in FIG. 10, in the release unit 140, the pressing tool 110 that has been pressed into the substrate sheet 2 is released. Specifically, the pressing tool 110 that has been pressed into the substrate sheet 2 is moved downward by the piston cylinder so as to withdraw the first projection mold 111 from the interior of the first protrusion portion 3 of the substrate sheet 2 and withdraw the second projection molds 112 from the interior of the second protrusion portions 4 (see FIG. 11(e)). After that, the strip-shaped substrate sheet 2 is cut into a unit length by a cutting means (not shown). In this way, an intended microprotrusion device 1 is obtained.

Figure 12A:
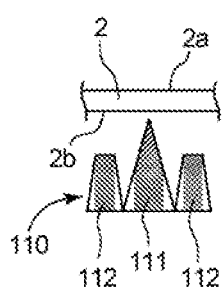
FIGS. 12(a) to 12(e) are illustrative diagrams showing principal steps of a method for producing a microprotrusion device according to another embodiment of the present invention.
Figure 12B:
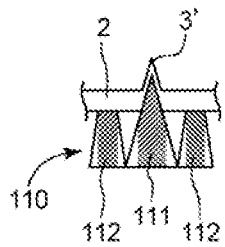
Figure 12C:
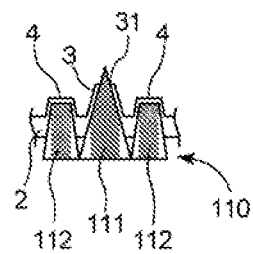
Figure 12D:
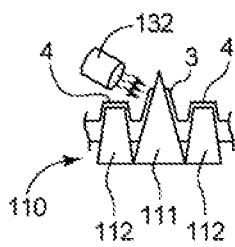
Figure 12E:
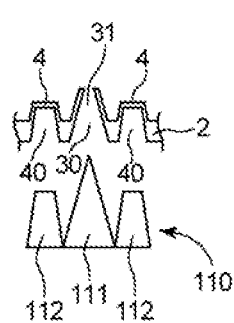

As the heating means included in the pressing tool 110, as described above, it is also possible to use a heat generating apparatus such as a heater apparatus. FIG. 12 shows a process of forming protrusion portions 3 and 4 in the case where a heat generating apparatus is used as the heating means. The step of forming protrusion portions 3 and 4 when a heat generating apparatus is used as the heating means is basically the same as that when the ultrasonic vibrator apparatus is used as the heating means. That is, as shown in FIG. 12(a), in a state in which the tip ends of the first projection mold 111 and the second projection molds 112 are directed toward the lower surface 2b of the substrate sheet 2, and the heating means (heat generating apparatus) is running, as shown in FIGS. 12(b) and 12(c), the pressing tool 110 is pressed from the lower surface 2b side of the substrate sheet 2 toward the upper surface 2a side, and the first and second pressing steps are carried out simultaneously with a single pressing operation of the pressing tool 110. After that, the cooling step in the cooling unit 130 and the releasing step of releasing the pressing state in the release unit 140 are sequentially carried out. The details that are not specifically described for a case where a heat generating apparatus is used as the heating means are the same as those when the ultrasonic vibrator apparatus is used as the heating means.

The first projection mold 111 and the second projection molds 112 themselves are heated by the heat generating apparatus, and pressed into the substrate sheet 2 while they are heated. From the viewpoint of facilitating the formation of protrusion portions 3 and 4, the heating temperature of the substrate sheet 2 by the projection molds 111 and 112 is preferably greater than or equal to the softening point of a thermoplastic resin constituting the substrate sheet 2, and more preferably less than the melting temperature of the thermoplastic resin.

The method for producing a microprotrusion device 1 described above is applicable not only to the production of a microprotrusion device 1A that has substantially the same shape as that of the microprotrusion device 1, but also to the production of microprotrusion devices 1B, 1C, and 1D. With this production method, it is possible to highly accurately form fine protrusion portions that have an opening at their tip end by simply performing a single pressing operation of the pressing tool, and mass produce microprotrusion devices in a stable manner with a simple process. As the pressing tool, it is possible to use a pressing tool that has a shape corresponding to the shape of the microprotrusion device that is the intended product, and the dimensions of the constituent elements of the pressing tool, the arrangement of the projection molds, and the like can be set to be the same as those of the microprotrusion device that is the intended product.

Up to here, the present invention has been described by way of preferred embodiments, but the present invention is not limited to the embodiments given above. For example, there is no particular limitation on the shape and arrangement of the protrusion portions 3 and 4, and the shape and arrangement of the protrusion portions 3 and 4 can be set arbitrarily. Also, in the embodiments of the production method according to the present invention, the substrate sheet (the first protrusion portion and the second protrusion portions) that has undergone the pressing step is forcibly cooled by a cooling apparatus, but may cool naturally without the use of a cooling apparatus.

Also, in the embodiments described above, the microneedles, or in other words, the microprotrusion portions all have a hollow structure, and the first protrusion portions have an opening portion at their tip end in the protruding direction, but the microprotrusion device according to the present invention is not limited thereto. It is possible to, for example, form a first protrusion portion having a solid structure by filling the hollow portion of a hollow microneedle-shaped first protrusion portion with a resin for forming the protrusion portion or a resin other than the resin for forming the protrusion portion. That is, the present invention encompasses "a microprotrusion device including a needle-like and solid first protrusion portion 3 that is formed so as to protrude from one surface 2a of a substrate sheet 2, and a hollow second protrusion portion 4 that is formed so as to protrude from a vicinity of the first protrusion portion 3 on the one surface 2a of the substrate sheet 2 and has a protrusion height lower than that of the first protrusion portion 3". A first protrusion portion that does not have an opening at its tip end can be obtained by adjusting the pressing speed and heating temperature of the first projection mold. However, the microprotrusion device preferably includes a first protrusion portion that has a hollow structure and an opening portion at its tip end as in the embodiments described above because a large amount of medicament can be retained and the medicament can be easily supplied into the body.

Also, in the embodiments described above, in both of the first and second pressing steps, the tip end of the first projection mold 111 or the second projection mold 112 is abutted against the lower surface 2b of the substrate sheet 2, and the abutment portion is heated by a heating means (an ultrasonic vibrator apparatus or a heat generating apparatus), during which the tip end is pressed toward the upper surface 2a side of the substrate sheet 2 by a predetermined distance so as to deform the pressed portion of the substrate sheet 2 into a shape of the first projection mold 111 or the second projection mold 112. That is, heating of the substrate sheet 2 by the heating means and pressing of the substrate sheet 2 by the projection mold are carried out simultaneously. However, it is unnecessary to simultaneously carry out these steps. The point is to press the first or second projection mold by a predetermined distance while the portion of the substrate sheet abutting against the first or second projection mold is heated directly or indirectly by the heating means. For example, it is also possible to use a method in which, in the first pressing step, the tip end of the first projection mold 111 is heated in advance by the heating means before the tip end of the first projection mold 111 is abutted against the lower surface 2b of the substrate sheet 2, and the heated tip end of the first projection mold 111 is then abutted against the lower surface 2b of the substrate sheet 2 so as to heat the abutment portion through the application of heat from the tip end of the first projection mold 111 without the use of the heating means, during which the tip end is pressed toward the upper surface 2a side of the substrate sheet 2 by a predetermined distance. The method of indirectly heating the substrate sheet by the heating means as described above may also be carried out in the second pressing step. With respect to the above-described embodiments according to the present invention, the following additional statements are further disclosed.

<1>

A method for producing a microprotrusion device including a needle-like and hollow first protrusion portion that is formed so as to protrude from one surface of a substrate sheet that can be softened through the application of heat, and a hollow second protrusion portion that is formed so as to protrude from the vicinity of the first protrusion portion on the one surface of the substrate sheet and has a protrusion height lower than that of the first protrusion portion, the method comprising:

a first pressing step of, with the use of a first projection mold for forming the first protrusion portion and a heating means for heating an object that is in contact with the first projection mold, abutting a tip end of the first projection mold against the other surface of the substrate sheet and heating the abutment portion, during which the first projection mold is pressed toward the one surface side of the substrate sheet by a predetermined distance so as to deform the pressed portion of the substrate sheet into a shape of the first projection mold; and a second pressing step of, with the use of a second projection mold for forming the second protrusion portion and a heating means for heating an object that is in contact with the second projection mold, abutting a tip end of the second projection mold against the other surface of the substrate sheet and heating the abutment portion, during which the second projection mold is pressed toward the one surface side of the substrate sheet by a predetermined distance so as to deform the pressed portion of the substrate sheet into a shape of the second projection mold, wherein a pressed distance of the substrate sheet pressed by the second projection mold is set to be shorter than a pressed distance of the substrate sheet pressed by the first projection mold.

<2>

The method for producing a microprotrusion device as set forth in clause <1>, wherein, in the first pressing step, the tip end of the first projection mold is abutted against the other surface of the substrate sheet and the abutment portion is heated by the heating means, during which the first projection mold is pressed toward the one surface side of the substrate sheet by a predetermined distance so as to deform the pressed portion of the substrate sheet into a shape of the first projection mold, and in the second pressing step, the tip end of the second projection mold is abutted against the other surface of the substrate sheet and the abutment portion is heated by the heating means, during which the second projection mold is pressed toward the one surface side of the substrate sheet by a predetermined distance so as to deform the pressed portion of the substrate sheet into a shape of the second projection mold.

<3>

The method for producing a microprotrusion device as set forth in clause <1> or <2>, wherein, with the use of a pressing tool including the first projection mold and the second projection mold formed on one surface of a substrate, the second projection mold having a protrusion height lower than that of the first projection mold, and a heating means that heats an object that is in contact with the first and second projection molds.

<4>

The method for producing a microprotrusion device as set forth in clause <3>, wherein, the first pressing step and the second pressing step are carried out simultaneously by pressing the pressing tool from the other surface side of the substrate sheet toward the one surface side of the substrate sheet while the tip ends of the first and second projection molds are directed toward the other surface of the substrate sheet and the heating means is running.

<5>

The method for producing a microprotrusion device as set forth in clause <4>, wherein the first pressing step and the second pressing step are carried out simultaneously with a single pressing operation of the pressing tool.

<6>

The method for producing a microprotrusion device as set forth in any one of clauses <3> to <5>, wherein a difference between a protrusion height of the first projection mold from the one surface of the substrate and a protrusion height of the second projection mold from the one surface of the substrate is smaller than a substantial thickness of the substrate sheet.

<7>

The method for producing a microprotrusion device as set forth in clause <1> or <2>, the method comprising the steps of:

carrying out the first pressing step by using a pressing tool that includes the first projection mold but does not include the second projection mold; and carrying out the second pressing step by using a pressing tool that includes the second projection mold but does not include the first projection mold, wherein the two pressing steps are carried out in an arbitrary order, and the substrate sheet is cooled after each pressing step has been carried out.

<8>

The method for producing a microprotrusion device as set forth in any one of clauses <1> to <7>, wherein the second projection mold has a truncated cone-shape.

<9>

The method for producing a microprotrusion device as set forth in any one of clauses <1> to <8>, wherein the heating means is a means for ultrasonically vibrating the first projection mold and the second projection mold, and the first and second projection molds ultrasonically vibrated through operation of the heating means are abutted against the substrate sheet so as to generate frictional heat at an abutment portion of the substrate sheet and soften the abutment portion.

<10>

The method for producing a microprotrusion device as set forth in any one of clauses <1> to <9>, wherein a heating temperature of the substrate sheet by the heating means is greater than or equal to a glass transition temperature of the substrate sheet and less than a melting point of the substrate sheet.

<11>

The method for producing a microprotrusion device as set forth in any one of clauses <1> to <10>, wherein a heating temperature of the substrate sheet heated by the heating means is greater than or equal to a softening temperature of the substrate sheet and less than a melting point of the substrate sheet.

<12>

The method for producing a microprotrusion device as set forth in any one of clauses <1> to <11>, wherein the microprotrusion device comprises a microneedle.

<13>

The method for producing a microprotrusion device as set forth in clause <12>, wherein the first protrusion portion and the second protrusion portion constitute a microneedle array that is disposed on the substrate sheet.

<14>

A microprotrusion device comprising:

needle-like first protrusion portions that are formed so as to protrude from one surface of a substrate sheet; and hollow second protrusion portions that are formed so as to protrude from the vicinity of the first protrusion portions on the one surface of the substrate sheet and have a protrusion height lower than that of the first protrusion portions.

<15>

The microprotrusion device as set forth in clause <14>, wherein the first protrusion portions are hollow and have an opening portion, and hollow portions of the first protrusion portions are in communication with the outside via the opening portion.

<16>

The microprotrusion device as set forth in clause <15>, wherein the opening portions are formed at tip ends of the first protrusion portions.

<17>

The microprotrusion device as set forth in clause <15> or <16>, wherein the hollow portions of the first protrusion portions function as reservoirs for a liquid that is to be discharged from the opening portions of the first protrusion portions to the outside.

<18>

The microprotrusion device as set forth in any one of clauses <14> to <17>, wherein each second protrusion portion does not have an opening portion on the one surface side of the substrate sheet.

<19>
The microprotrusion device as set forth in any one of clauses <14> to <18>,
wherein a tip end of each second protrusion portion has a horizontally extending straight line or a curve projecting in a protruding direction of the second protrusion portion as viewed in side view.
<20>
The microprotrusion device as set forth in any one of clauses <14> to <19>, comprising
an area that is in the vicinity of a single first protrusion portion and in which a pair of second protrusion portions are disposed at opposing positions with the single first protrusion portion interposed therebetween.
<21>
The microprotrusion device as set forth in any one of clauses <14> to <20>,
wherein a single first protrusion portion and the second protrusions provided in the vicinity of the single first protrusion portion are connected at their root portions.
<22>
The microprotrusion device as set forth in any one of clauses <14> to <20>,
wherein, as viewed from above, the first protrusion portions and the second protrusion portions are disposed radially around a single first protrusion portion, and in at least one of the plurality of radial directions, the first protrusion portions and the second protrusion portions are alternately provided.
<23>
The microprotrusion device as set forth in any one of clauses <14> to <22>,
wherein the second protrusion portions have a continuous annular shape or a discontinuous annular shape as viewed from above.
<24>
The microprotrusion device as set forth in any one of clauses <14> to <23>,
wherein a difference between a protrusion height of the first protrusion portions from the one surface of the substrate sheet and a protrusion height of the second protrusion portions from the one surface of the substrate sheet is smaller than a substantial thickness of the substrate sheet.
<25>
The microprotrusion device as set forth in any one of clauses <14> to <24>,
wherein the first protrusion portions are microneedles.
<26>
The microprotrusion device as set forth in clause <25>,
wherein the first protrusion portions and the second protrusion portions constitute a microneedle array that is disposed on the substrate sheet.

EXAMPLES

Hereinafter, the present invention will be described in further detail by way of examples, but the present invention is not limited to the examples given below.

Production Example 1

A microprotrusion device 1 was produced by using the production apparatus 100 shown in FIG. 10. As the substrate sheet, a 0.3 mm thick sheet made of polyglycolic acid was used. The pressing tool 110 that was used to produce the microprotrusion device 1 included a circular cone-shaped first projection mold 111 and truncated cone-shaped second projection molds 112 that were formed on the upper surface of a substrate 113, and an ultrasonic vibrator apparatus for ultrasonically vibrating the projection molds 111 and 112. The first projection mold 111 had a protrusion height from the upper surface of the substrate 113 of 3 mm, and a tip end diameter of 0.015 mm, and the second projection molds 112 had a protrusion height from the upper surface of the substrate 113 of 2.78 mm, and a tip end diameter of 0.5 mm. The pressed distance of the substrate sheet pressed by the first projection mold was 0.85 mm [=0.55 mm (the height of the first protrusion portion)+0.3 mm (the substantial thickness of the substrate sheet)], and the pressed distance of the substrate sheet pressed by the second projection molds was 0.63 mm [=0.33 mm (the height of the second protrusion portion)+0.3 mm (the substantial thickness of the substrate sheet)]. The height difference between the first protrusion portion and the second protrusion portions was 0.22 mm.

Reference Production Example 1

A microprotrusion device was produced in the same manner as in Production Example 1 except that, instead of the pressing tool 110 including two different types of projection molds 111 and 112 having different protrusion heights, a pressing tool including only one type of projection mold, or in other words, a circular cone-shaped projection mold was used. The pressing tool used in Reference Production Example 1 was the same as that used in Production Example 1 except that the pressing tool included the first projection mold 111 but did not include the second projection molds 112. The pressed distance of the substrate sheet pressed by the pressing tool was 0.5 mm [=0.2 mm (the height of the first protrusion portion)+0.3 mm (the substantial thickness of the substrate sheet)].

Evaluation

Figure 11E:
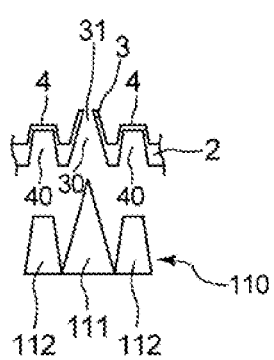

The microprotrusion device 1 produced in Production Example 1 was visually observed, and it was found that the first protrusion portion 3 formed by pressing the first projection mold 111 having a circular cone-shape had an opening portion 31 formed at its tip end (see FIG. 11(e)). However, in the microprotrusion device obtained in Reference Production Example 1, the protrusion portion did not have an opening at its tip end despite the fact that (the amount of movement of the first projection mold–the amount of movement of the second projection mold) in Production Example 1 and that in Reference Production Example 1 were substantially the same. From this, it can be seen that by using a pressing device including a plurality of types of projection molds of different protrusion heights, it is possible to perform control such that the penetration depth into the skin is shallow, and easily form fine microneedles that have an opening at their tip end, which was deemed as being difficult to achieve. That is, it is possible to easily form protrusion portions having a desired shape while performing control such that the penetration depth into the skin is shallow

INDUSTRIAL APPLICABILITY

According to the present invention, it is possible to provide a microprotrusion device including microprotrusions, wherein it is possible to control the depth of penetration into the skin and cause less pain when the microprotrusions penetrate the skin. Also, according to the present invention, it is possible to provide a method for producing such a microprotrusion device at a relatively low cost and in a stable manner.

The invention claimed is:

1. A microprotrusion device comprising:
   needle-like first protrusion portions that are formed so as to protrude from one surface of a substrate sheet, wherein said first protrusion portions are hollow and each has an opening portion, the hollow portions of the first protrusion portions being in communication with the outside of the device via the opening portions of the first protrusion portions, wherein the hollow portions of the first protrusion portions function as reservoirs for a liquid that is to be discharged from the opening portions of the first protrusion portions to the outside of the device; and
   second protrusion portions that are formed so as to protrude from the vicinity of the first protrusion portions on the one surface of the substrate sheet and to have a protrusion height lower than that of the first protrusion portions, said second protrusion portions not having openings on said one surface of the substrate sheet.

2. The microprotrusion device according to claim 1, wherein the opening portions are formed at tip ends of the first protrusion portions.

3. The microprotrusion device according to claim 1, wherein a tip end of each second protrusion portion has a horizontally extending straight line or a curve projecting in a protruding direction of the second protrusion portion as viewed in side view.

4. The microprotrusion device according to claim 1, comprising
   an area that is in the vicinity of a single first protrusion portion and in which a pair of second protrusion portions are disposed at opposing positions with the single first protrusion portion interposed therebetween.

5. The microprotrusion device according to claim 1, wherein a single first protrusion portion and the second protrusions provided in the vicinity of the single first protrusion portion are connected at their base portions.

6. The microprotrusion device according to claim 1, wherein, as viewed from above, the first protrusion portions and the second protrusion portions are disposed radially around a single first protrusion portion, and in at least one of the plurality of radial directions, the first protrusion portions and the second protrusion portions are alternately provided.

7. The microprotrusion device according to claim 1, wherein the second protrusion portions have a continuous annular shape or a discontinuous annular shape as viewed from above.

8. The microprotrusion device according to claim 1, wherein a difference between a protrusion height of the first protrusion portions from the one surface of the substrate sheet and a protrusion height of the second protrusion portions from the one surface of the substrate sheet is smaller than a substantial thickness of the substrate sheet.

9. The microprotrusion device according to claim 1, wherein the first protrusion portions are microneedles.

10. The microprotrusion device according to claim 9, wherein the first protrusion portions and the second protrusion portions constitute a microneedle array that is disposed on the substrate sheet.

11. A microprotrusion device comprising:
    needle-like first protrusion portions that are formed so as to protrude from one surface of a substrate sheet, wherein said first protrusion portions are hollow and each has an opening portion, the hollow portions of the first protrusion portions being in communication with the outside of the device via the opening portions of the first protrusion portions, wherein the hollow portions of the first protrusion portions function as reservoirs for a liquid that is to be discharged from the opening portions of the first protrusion portions to the outside of the device; and
    second protrusion portions that are formed so as to protrude from the vicinity of the first protrusion portions on the one surface of the substrate sheet and to have a protrusion height lower than that of the first protrusion portions, and wherein a tip end of each second protrusion portion has a horizontally extending straight line or a curve projecting in a protruding direction of the second protrusion portion as viewed in side view.

* * * * *